(12) United States Patent
Yuan et al.

(10) Patent No.: US 10,745,342 B2
(45) Date of Patent: Aug. 18, 2020

(54) SYNTHESIS METHOD OF 2,4,6-TRIFLUOROBENZYLAMINE

(71) Applicants: ZHEJIANG ZHONGXIN FLUORIDE MATERIALS CO., LTD., Shaoxing (CN); SHAOXING ZHONGKE BAIYUN CHEMICAL TECHNOLOGY CO., LTD., Shaoxing (CN)

(72) Inventors: Qiliang Yuan, Shaoxing (CN); Jie Qian, Shaoxing (CN); Xin Lai, Shaoxing (CN); Haifeng Chen, Shaoxing (CN); Yinhao Chen, Shaoxing (CN); Chao Wang, Shaoxing (CN)

(*) Notice: Subject to any disclaimer, the term of this patent is extended or adjusted under 35 U.S.C. 154(b) by 0 days.

(21) Appl. No.: 16/812,385

(22) Filed: Mar. 9, 2020

(65) Prior Publication Data

US 2020/0207702 A1 Jul. 2, 2020

Related U.S. Application Data

(63) Continuation of application No. PCT/CN2019/072276, filed on Jan. 18, 2019.

(30) Foreign Application Priority Data

Jul. 5, 2018 (CN) .......................... 2018 1 0727808

(51) Int. Cl.
- *C07C 209/48* (2006.01)
- *C07C 209/74* (2006.01)
- *B01J 21/18* (2006.01)
- *B01J 31/28* (2006.01)
- *B01J 23/44* (2006.01)
- *C07C 255/50* (2006.01)
- *C07C 211/29* (2006.01)

(52) U.S. Cl.
CPC ............. *C07C 209/48* (2013.01); *B01J 21/18* (2013.01); *B01J 23/44* (2013.01); *B01J 31/28* (2013.01); *C07C 209/74* (2013.01); *C07C 255/50* (2013.01); *C07C 211/29* (2013.01)

(58) Field of Classification Search
CPC ... C07C 209/48; C07C 209/74; C07C 211/29; C07C 255/50; B01J 23/44; B01J 21/18; B01J 31/28
See application file for complete search history.

(56) References Cited

U.S. PATENT DOCUMENTS

| | | |
|---|---|---|
| 10,513,436 B1 | 12/2019 | Siriwardane et al. |
| 2020/0039836 A1 | 2/2020 | Richardson et al. |
| 2020/0043465 A1 | 2/2020 | Yang et al. |

FOREIGN PATENT DOCUMENTS

| | | |
|---|---|---|
| CN | 101412660 A | 4/2009 |
| CN | 107778183 A | 3/2018 |
| CN | 108586267 A | 9/2018 |

OTHER PUBLICATIONS

Internation Search Report of PCT/CN2019/072276, dated Jan. 18, 2019.

*Primary Examiner* — Jafar F Parsa
(74) *Attorney, Agent, or Firm* — Erson IP (Nelson IP)

(57) ABSTRACT

The disclosure provides a synthesis method of 2,4,6-trifluorobenzylamine, belonging to the technical field of chemical synthesis. The synthesis method is characterized by comprising the following steps: (1) allowing pentachlorobenzonitrile as a raw material to undergo fluoridation reaction with a fluoridation agent based on 2,4,6-trifluoro-3,5-dichlorobenzonitrile as a solvent to obtain 2,4,6-trifluoro-3,5-dichlorobenzonitrile; (2) hydrogenating the obtained 2,4,6-trifluoro-3,5-dichlorobenzonitrile with hydrogen in the presence of organic carboxylic acid, based, on palladium carbon as a catalyst to obtain 2,4,6-trifluoro-3,5-dichlorobenzylamine; and (3) hydrogenating the obtained 2,4,6-trifluoro-3,5-dichlorobenzylamine with hydrogen in a solvent in the presence of a catalyst to obtain 2,4,6-trifluorobenzylamine. The synthesis method has the advantages of low raw material cost, short reaction steps, high reaction yield, good product purity simple operation and the like, and is suitable for industrial production.

11 Claims, No Drawings

SYNTHESIS METHOD OF 2,4,6-TRIFLUOROBENZYLAMINE

CROSS-REFERENCE TO RELATED APPLICATIONS

This application is a continuation of International Patent Application No. PCT/CN2019/072276 with a filing date of Jan. 8, 2019, designating the United States, now pending, and further claims priority to Chinese Patent Application No. 2018107278088 with a filing date of Jul. 5, 2018. The content of the aforementioned applications, including any intervening amendments thereto, are incorporated herein by reference.

TECHNICAL FIELD

The disclosure belongs to the technical field of chemical synthesis, and particularly relates to a synthesis method of 2,4,6-trifluorobenzylamine.

BACKGROUD OF THE PRESENT INVENTION 2,4,6-trifluorobenzylamine is an important fine chemicals, has a wide application prospect in the fields of drug synthesis and the like, and is a key intermediate for synthesizing Bictegravir (GS-9883).

There are three methods for synthesizing 2,4,6-trifluorobenzylamine, which have been disclosed at present, as follows:

(1) patent CN104610068 discloses that 2,4,6-trifluorobenzylamine is synthesized by using 1,3,5-trifluorobenzene as a raw material via lithiation, formylation, reduction, chlorination, ammoniation and other reactions.

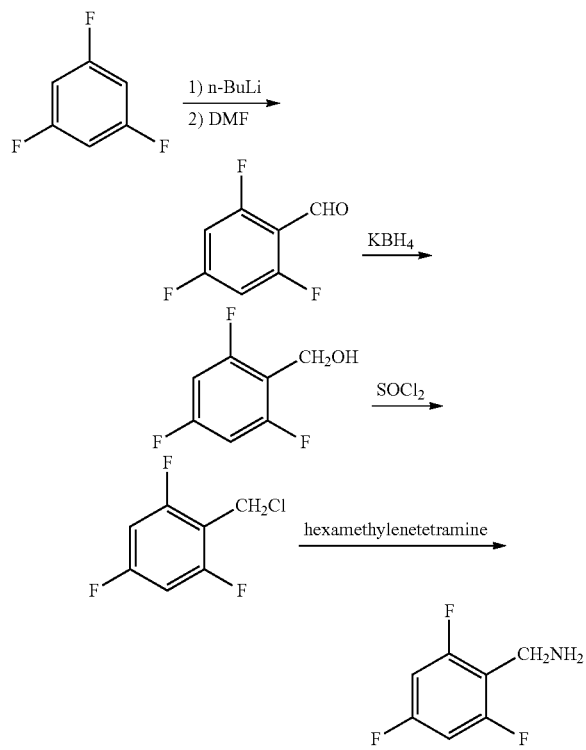

This synthesis method is long in reaction steps, complicated in operation conditions and expensive in raw and auxiliary materials, has a large amount of three wastes in the process of synthesis, and thus is lack of industrial application values.

(2) Patent CN106349083 discloses 2,4,6-trifluorobenzylamine is synthesized by using 2,4,6-trifluorobenzonitrile as a raw material through one-step hydrogenation.

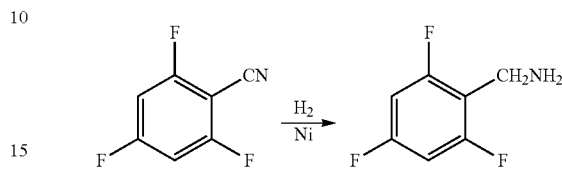

This synthesis method has only one-step reaction, however, the raw material 2,4,6-trifluorobenzonitrile is expensive in price and not available. Therefore, this synthesis method cannot be applied on large scale.

(3) Patent CN107778183 discloses that 2,4,6-trifluorobenzylamine is synthesized by using trifluorobenzonitrile as a raw material through fluorination, reduction and other steps.

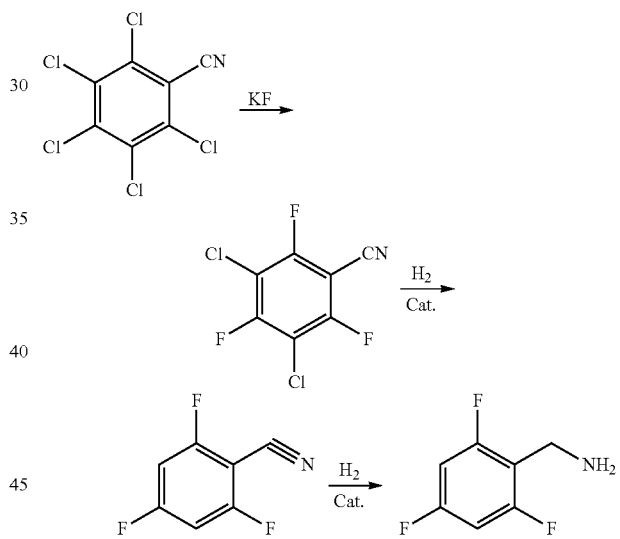

This synthesis method is cheap and available in raw material and short in reaction steps, but complicated in operation process, many in side reactions and undesirable in reaction yield. Therefore, industrial application of this synthesis method is restrained.

SUMMARY OF PRESENT INVENTION

The objective of the disclosure is to provide a synthesis method of 2,4,6-trifluorobenzylamine, which is low in raw material cost, short in reaction steps, high in reaction yield, good in product purity, simple to operate and suitable for industrial production.

The technical solution adopted by the disclosure is as follows:

Provided is a synthesis method of 2,4,6-trifluorobenzylamine, comprising the following steps:

(1) allowing pentachlorobenzonitrile as a raw material to undergo fluoridation reaction with a fluoridation agent based on 2,4,6-trifluoro-3,5-dichlorobenzonitrile as a solvent to obtain 2,4,6-trifluoro-3,5-dichlorobenzonitrile;

(2) hydrogenating the obtained 2,4,6-trifluoro-3,5-dichlorobenzonitrile (II) with hydrogen in the presence of organic carboxylic acid based on palladium carbon as a catalyst to obtain 2,4,6-trifluoro-3,5-dichlorobenzylamine (III); and (3) hydrogenating 2,4,6-trifluoro-3,5-dichlorobenzylamine (III) obtained in step (2) with hydrogen in a solvent in the presence of a catalyst to obtain 2,4,6-trifluorobenzylamine (IV).

The synthesis route adopted by the disclosure can be represented using the following reaction formula:

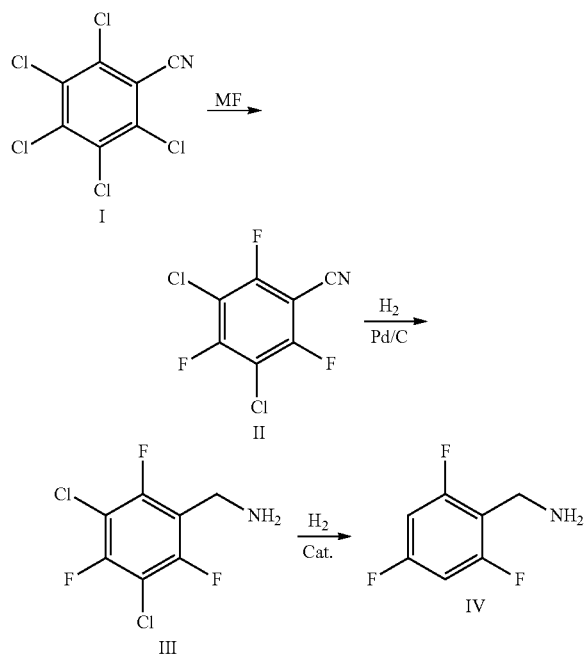

The disclosure can also further set as follows:
in step (1):
the reaction in this step belongs to halogen exchange fluoridation reaction, and selection of the solvent has important influence on whether the reaction can be smoothly performed. The common solvents for halogen exchange fluoridation reaction are mostly polar non-proton solvents, mainly including: N,N-dimethylformamide, N,N-dimethylacetamide, N-methylpyrrolidone, 1,3-dimethyl-2-imidazolinone, dimethylsulfoxide, dimethylsulfone and sulfolane. However, introduction of solvents not only increases types of materials but also needs to increases operations such as solvent removal and solvent recovery, thereby leading to complicated operation process and increased synthesis cost. Considering the product 2,4,6-trifluoro-3,5-dichlorobenzonitrile in step (1), it is a polar non-proton compound, which is liquid at room temperature and has a boiling point of about 230° C. Through thermal stability measurement via a differential scanning calorimeter, it can be determined that the product 2,4,6-trifluoro-3,5-dichlorobenzonitrile has stable chemical property within 300° C. and meets requirements as the solvent in step (1), and good results are gained after research on 2,4,6-trifluoro-3,5-dichlorobenzonitrile used as the reaction solvent. Therefore, 2,4,6-trifluoro-3,5-dichlorobenzonitrile is used as the reaction solvent, and the amount of 2,4,6-trifluoro-3,5-diclhlorobenzonitrile is 15 times the mass of the compound (I).

The fluoridation agent refers to an alkaline metal fluoride salt such as lithium fluoride, sodium fluoride, potassium fluoride, rubidium fluoride and cesium fluoride. Comprehensively considering factors such as activity and cost of the fluoridation agent, the preferred fluoridation agent is one or two of sodium fluoride and potassium fluoride. The molar ratio of the fluoridation agent to the compound (I) is (3:1)~(6:1).

In the process of fluoridation reaction, addition of a proper amount of single or compounded catalyst is beneficial to improvement of fluoridation reaction rate and reduction of fluoridation temperature. There are many types of optional catalysts, for example, quaternary ammonium salt catalysts such as tetrabutylammonium bromide, tetrabutylammonium chloride, tetrabutylammonium fluoride, benzyltriethylammonium chloride and hexadecyltrimethylammonium chloride, quaternary phosphonium salt catalysts such as triphenylmethylphosphonium bromide, triphenylethylphosphonium bromide, tetraphenylphosphonium bromide, and crown ether catalysts such as 18-crown-6 and 15-crown-5. The amount of the catalyst is 0~0.5 times the mass of the compound (I).

Reaction activities of fluoridation reaction systems consisting of types and amounts of different fluoridation agent, types and amounts of different catalyst and amounts of different solvent are mutually varied, and thus fluoridation reaction temperatures are different. Generally, when the fluoridation reaction temperature is less than 150° C., and the fluoridation reaction speed is slow, which is not beneficial to improvement of synthesis efficiency, when the fluoridation reaction temperature is more than 250° C., excessive fluoridation side reaction will rapidly increase with rising of the reaction temperature. In addition, high-temperature decomposition side reaction of compounds such as fluoridation products and intermediates can also increase, leading to a fact that the reaction system becomes complicated, and the reaction yield and product purity can rapidly decrease. Thus, in order to obtain a proper reaction speed and meanwhile inhibit generation of side reactions such as excessive fluoridation and high temperature decomposition to the greatest extent, the fluoridation reaction temperature typically selects 150~250° C., and the preferred fluoridation reaction temperature is 170~240° C.

After the fluorination reaction is ended, the reaction system can be posttreated using many methods to obtain 2,4,6-trifluoro-3,5-dichlorobenzonitrile (including a fluorinated product and added reaction solvents, both of which are the same compound). The optional post-treatment methods are as follows: 1, a vacuum distillation method in which the compound (II) is evaporated from the system until it is completely evaporated to be dryness, and the obtained fraction is 2,4,6-trifluoro-3,5-dichlorobenzonitrile; 2, a filtration method in which the compound (II) is separated from the inorganic salt to obtain 2,4,6-trifluoro-3,5-dichlorobenzonitrile; 3, a manner in which 2,4,6-trifluoro-3,5-dichlorobenzonitrile is obtained by firstly dissolving the inorganic salt with water and then layering via standing; 4, a manner in which 2,4,6-trifluoro-3,5-dichlorobenzonitrile is obtained by adding a proper organic solvent to dilute the system, then filtering to separate the inorganic salt from the system and distilling the filtrate to remove the solvent; 5, a manner in which 2,4,6-trifluoro-3,5-dichlorobenzonitrile is obtained by dissolving the inorganic salt with water, then extracting with, a proper organic solvent, carrying out drying, distillation and other operations on extract liquor. Of course, 2,4,6-trifluoro-3,5-dichlorobenzonitrile is obtained by using other proper post-treatment methods. The preferred posttreatment methods are 1~3, which facilitate the reduction of types of materials used in the process of synthesis because new organic solvents are not introduced, thereby simplifying operation process and reducing synthesis cost.

In step (2):

The used organic acid refers to C1~C10 linear or branched monobasic or binary alkyl carboxylic acid, monobasic or binary aryl carboxylic acid, specifically for example, formic acid, acetic acid, propionic acid, n-butyric acid, iso-butyric acid, n-pentanoic acid, iso-pentanoic acid, hexanoic acid, heptanoic acid, caprylic acid, nonanoic acid, capric acid, oxalic acid, malonic acid, succinic acid, glutaric acid, adipic acid, pimelic acid, octanedioic acid, azelaic acid, sebacic acid, benzoic acid, p-toluylic acid, phthalic acid and terephthalic acid. Comprehensively considering factors such as cost, the preferred organic carboxylic acid is C1~C10 linear or branched monobasic organic carboxylic acid, specifically for example, formic acid, acetic acid, propionic acid, n-butyric acid, iso-butyric acid, n-pentanoic acid, iso-pentanoic acid, hexanoic acid, heptanoic acid, caprylic acid, nonanoic acid and decanoic acid. The optimal organic carboxylic acid is selected from one or more of formic acid, acetic acid, propionic acid, n-butyric acid, iso-butyric acid, n-pentanoic acid and iso-pentanoic acid. The main function of organic carboxylic acid in the reaction process is to generate corresponding carboxylate with the reduction product 2,4,6-trifluoro-3,5-dichlorobenzylamine, thereby avoiding the generation of reductive amination side reaction between the organic pentanoic and the reduction intermediate 2,4,6-trifluoro-3,5-dichlorobenzylimine.

The reaction needs to be carried out in appropriate solvents. The optional solvent includes ester solvents such as methyl acetate, ethyl acetate and propyl acetate, ether solvents such as tetrahydrofuran, 2-methyltetrahydrofuran, alcohol solvents such as methanol, ethanol and isopropanol, and water. When one or more of formic acid, acetic acid, propionic acid, n-butyric acid, isobutyric acid, n-pentanoic acid and isopentanoic acid, are used as organic carboxylic acid, these organic carboxylic acids can also be used as the reaction solvents. Furthermore, when the organic carboxylic acid and the reaction solvent are the same compound, the reaction has great advantages in production due to reduced material types, simplified production operations, convenient solvent recovery and other reasons. Therefore one or more of formic acid, acetic acid, propionic acid, n-butyric acid, iso-butyric acid, n-pentanoic acid and iso-pentanoic acid are preferably selected as not only organic carboxylic acids but also reaction solvents, and the amount is 1~20 times of the mass of the compound (II).

The palladium carbon refers to an active carbon dispersion substance of palladium obtained by loading metal palladium on, active carbon, which has catalytic hydrogenation activity. Palladium carbon can be self-made or commercial products of different specifications can be used. According to the effective content and moisture content of palladium, palladium carbon can be divided into many different specifications, such as 10% dry palladium carbon, 10% wet palladium carbon (moisture content is about 50%), 5% dry palladium, carbon, 5% wet palladium carbon (moisture content is about 50%), 1% dry palladium carbon and 1% wet palladium carbon (moisture content is about 50%). The palladium carbon has no clear limitation on the specification, as long as the catalytic activity meets the requirements. The amount of palladium carbon as the catalyst is related to the effective content of palladium in palladium carbon. If 10% palladium carbon is used as the catalyst, the amount is 0.001-0.15 times of the mass of the compound (II) after deducting water (i.e., drying); if 5% palladium carbon is used as the catalyst, the amount is 0.001-0.2 times of the mass of the compound (II) after deducting water (i.e., drying); if 1% palladium carbon is used as the catalyst, the amount is 0.001-0.25 times of the mass of compound (II) after deducting water (i.e., drying). If other palladium carbon having effective palladium content is used, its amount will accordingly change, and the specific amount needs to be confirmed by experiments.

Hydrogenation pressure refers to the sum of partial pressures of various gases in a reactor under certain hydrogenation conditions such as certain feeding ratio and reaction temperature, including the sum of partial pressure of hydrogen, partial pressure of raw material steam and partial pressure of a solvent steam under such conditions. Under fixed conditions, the hydrogenation pressure can indirectly represent the partial pressure of hydrogen in the reactor. The hydrogenation pressure has an important influence on the hydrogenation reduction rate and the selection of hydrogenation equipment. If the hydrogenation pressure is low, the hydrogenation speed is slow, but requirements on hydrogenation equipment is relatively low; if the hydrogenation pressure is high, the hydrogenation speed is quick, but requirements on hydrogenation equipment and safe operation increase. The preferred hydrogenation pressure is 0.01~3.0 MPa.

The selection of hydrogenation temperature should consider not only hydrogenation reduction reaction rate but also inhibition of side reactions. If a relatively high hydrogenation temperature is used, although the hydrogenation reduction reaction rate is relatively fast and even a part of 2,4,6-trifluoro-3,5-dichlorobenzylamine is dehydrochlorinated to produce 2,4,6-trifluoro-3-chlorobenzylamine and 2,4,6-trifluorobenzylamine, a series of side reaction still occur, such as amidation side reaction between 2,4,6-trifluoro-3,5-dichlorobenzylamine and organic carboxylic acid, amidation side reaction between 2,4,6-trifluoro-3-chloroberizylamine and organic carboxylic acid and amidation side reaction between 2,4,6-trifluorobenzylamine and organic carboxylic acid. Thus, the hydrogenation reaction temperature should not be too high, and the preferred hydrogenation temperature range is 0~70° C.

After the hydrogenation reaction is ended, by simple post-treatment operations, such as filtering the reaction liquid to recover palladium carbon and distilling to recover the solvents, the 2,4,6-trifluoro-3,5-dichlorobenzylamine crude product can be obtained, which can be directly used for the reaction in step (3), or the obtained crude product 2,4,6-trifluoro-3,5-dichlorobenzylamine is properly purified to obtain 2,4,6-trifluoro-3,5-dichlorobenzylamine having higher purity. The selected post-treatment methods are as follows: 1, the reaction liquid in step (2) is filtered to recover palladium carbon, the filtrate is distilled to recover the solvent, and the concentrate is distilled to undergo the reaction in step (3): 2, the reaction liquid in step (2) is filtered to recover palladium carbon, the filtrate is distilled to recover the solvent, and the concentrate is distilled and subjected to alkali adjustment, layering, extraction, concentration and other operations to obtain the 2,4,6-trifluoro-3, 5-dichlorobenzylamine crude product which, undergoes the reaction in step (3); 3, the reaction solution in step (2) is filtered to recover palladium carbon, the filtrate is distilled to recover the solvent, and the distilled concentrate is subjected to alkali adjustment, layering, extraction, concentration and other operations to obtain the 2,4,6-trifluoro-3,5-dichlorobenzylamine pure product which undergoes the reaction in step (3); 4, the reaction solution in step (2) is distilled to recover the solvent, the concentrate is dissolved and distilled using the reaction solvent in step (3) and then filtered to recover the solvent, and the filtrate is used for the reaction of step (3); 5, the reaction solution in step (2) is distilled to recover the solvent, and the concentrate is distilled and directly subjected to the reaction of step (3) without recovery of palladium carbon. Of course, other appropriate posttreatment methods can also be selected. Palladium carbon and solvents recovered through posttreatment can be reused in step (2) after proper treatment.

In step (3):

The solvent is selected from one or more of ester solvents such as methyl acetate, ethyl acetate and propyl acetate, ether solvents such as tetrahydrofuran and 2-methyltetrahydrofuran, alcohol solvents such as, methanol, ethanol, n-propanol, iso-propanol, n-butanol, iso-butanol and tert-butanol, and water. The preferred solvents are alcohol solvents and water, which are selected from one or more of water, methanol, ethanol, n-propanol, iso-propanol, n-butanol, iso-butanoland tert-butanol. The amount of the solvent is 1-15 times of the mass of the compound (III).

The catalyst is selected from one or two of palladium carbon and spongy nickel. For the palladium carbon catalyst, it refers to the active carbon dispersion substance of palladium obtained by loading metal palladium on active carbon. According to the effective content of palladium and water content, it can be divided into many different specifications, such as 10% dry palladium carbon, 10% wet palladium carbon (water content is about 50%), 5% dry palladium carbon, 5% wet palladium carbon (water content is about 50%), 1% dry palladium carbon, 1% wet palladium carbon (water content is about 50%) and the like. For the spongy nickel catalyst, it is also called skeleton nickel or Rani nickel, which is microporous metal nickel left after nickel aluminum alloy is treated using alkali such as concentrated sodium hydroxide solution and concentrated potassium hydroxide solution to dissolve aluminum therein. Due to its active nature, this metal nickel can be burnt when being exposed to air, and thus is immersed in water for storage. The catalysts can be self-made or commercial products of different specifications can be used. The selection of catalysts has no definite limitation to the specifications, as long as the catalytic activity meets the requirements. For the palladium carbon catalyst, its amount is related to the effective content of palladium in palladium carbon. If 10% palladium carbon is used as the catalyst, its amount is 0.001-0.15 times of the mass of the compound (III) after deducting water (i.e., drying); if 5% palladium carbon is used as the catalyst, its amount is 0.001-0.2 times of the mass of the compound (III) after deducting water (i.e., drying); if 1% palladium carbon is used as the catalyst, its amount is 0.001-0.25 times of the mass of the compound (III) after deducting water (i.e., drying). If other palladium carbon catalysts having effective palladium contents are used, the amounts will accordingly change, and the specific amount needs to be confirmed by experiments. For the spongy nickel catalyst, it is a water-containing paste material whose amount is 0.01-0.3 times of the mass of the compound (III).

The reaction in this step is aromatic-ring hydrodechlorination reaction in which hydrogen chloride is generated. Because the hydrogenation equipment used in the production is mostly made of stainless steel, it can not withstand the corrosion of hydrogen chloride. In addition, the catalyst spongy nickel can react with hydrogen chloride to generate nickel chloride, which leads to the failure of the catalyst. Therefore, in order to avoid the adverse effect of the generated hydrogen chloride on the hydrogenation equipment and the spongy nickel catalyst, an appropriate amount of acid binding agent should be added in the process of reaction to neutralize the generated hydrogen chloride. Of course, if the reaction equipment with corrosion resistance ability is selected, and palladium carbon is selected as the catalyst, the acid binding agent may not be used for reaction. The acid binding agent can be hydroxide, oxide, phosphate and carbonate of alkali metal and alkali earth metal or the, like, or organic tertiary amine compounds can be used. The preferred acid binding agent is one or more of lithium hydroxide, sodium hydroxide, potassium hydroxide, magnesium hydroxide, calcium hydroxide, magnesium oxide, lithium phosphate, sodium phosphate, potassium carbonate, lithium carbonate, sodium carbonate, potassium carbonate, triethylamine, tri-n-propylamine, tri-n-butylamine, diethylisopropylamine, diisopropylethylamine, triethylenediamine, N-methylmorpholine, N,N-dimethylpiperazine and pyridine. The amount of the acid binding agent is determined according to the acid binding ability of the acid binding agent molecule. Based on a fact that hydrogen chloride generated in the reaction can completely be neutralized as a standard, the molar ratio of the preferred acid binding agent to the compound (III) is (0.5:1)~(4:1).

Hydrogenation pressure refers to the sum of partial pressures of various gases in a reactor under certain hydrogenation conditions such as certain feeding ratio and reaction temperature, including the sum of partial pressure of hydrogen, partial pressure of raw material steam and partial pressure of a solvent steam under such conditions. Under fixed conditions, the hydrogenation pressure can indirectly represent the partial pressure of hydrogen in the reactor. The hydrogenation, pressure has an important influence on the hydrogenation reduction rate and the selection of hydrogenation equipment. If the hydrogenation pressure is low, the hydrogenation speed is slow, but requirements on hydrogenation equipment are relatively low; if the hydrogenation pressure is high, the hydrogenation speed is quick, but requirements on hydrogenation equipment and safe operation increase. The preferred hydrogenation pressure is 0.01~3.0 MPa.

The selection of hydrogenation temperature is related to the hydrogenation system, such as reaction solvent, catalyst type and amount and hydrogenation pressure. The preferred hydrogenation temperature range is 0~100° C.

Compared with the prior art, the disclosure has the following beneficial effects:

(1) in the fluorination reaction step, the fluorination product 2,4,6-trifluoro-3,5-dichlorobenzonitrile serves as the reaction solvent, avoiding the use of other solvents, eliminating the operation of removing the solvent after the fluorination reaction is ended, simplifying the production process and reducing the production cost.

(2) Compared with the technical solution that aromatic ring hydrodechlorination is firstly carried out and then the cyano is hydrogenated and reduced to aminomethyl or one-pot method that hydrodechlorination and cyano reduction reaction are simultaneously carried out, the disclosure adopts a technical solution that the cyano is firstly hydrogenated and reduced to the aminomethyl and then aromatic-ring hydrodechlorination is carried out, which can effectively avoid that reduction-like amination side reaction occurs between amination in the process of reducing cyano into aminomethyl, thereby greatly improving the reaction yield.

(3) 2,4,6-trifluorobenzylamine is synthesized by three steps of fluorination, cyano reduction and reductive dechlorination based on pentachlorobenzonitrile as a raw material. The total yield of the reaction is more than 80% and the purity of the product is more than 99%. The disclosure has obvious advantages compared with the prior art The disclosure will be further described in combination with embodiments. It should be noted that the following embodiments are only used to help understanding the disclosure and do not limit the disclosure. The embodiments cannot contain all of the technical features, as long as the technical features involved in the specification do not conflict with each other, they can be combined with each other to form new embodiments.

DETAILED DESCRIPTION OF PREFERRED EMBODIMENTS

Example 1

90 g of pentachlorobenzonitrile, 270 g of 2,4,6-trifluoro-3,5-dichlorobenzonitrile, 69 g of potassium fluoride and 9 g of cetyltrimethylammonium chloride were added into a 500 ml dry reaction bottle, stirred, heated to 180-190° C. preserved and reacted for 20 h, the reaction was stopped and cooled. When the internal temperature was dropped to less than 80° C., vacuum distillation was carried out until the system was completely evaporated to dryness, so as to obtain 342.5 g of 2,4,6-trifluoro-3,5-dichlorobenzonitrile in total. After the solvent was removed, 72.5 g of 2,4,6-trifluoro-3,5-dichlorobenzonitrile was actually obtained. The yield was 98.2% and the purity was 98.7%.

Example 2

70 g of pentachlorobenzonitrile, 140 g of 2,4,6-trifluoro-3,5-dichlorobenzonitrile, 47.5 g of potassium fluoride and 14 g of tetraphenylphosphonium bromide were added into a 500 ml dry reaction bottle, stirred, heated to 200~210° C., preserved and reacted for 24 h, the reaction was stopped and cooled. After room temperature was reached, 150 g of water was added, stirred for 30 min at room temperature, and a lower-layer organic phase, namely, 196.5 g of 2,4,6-trifluoro-3,5-dichlorobenzonitrile, was separated by standing. After the solvent was removed, 56.5 g of 2,4,6-trifluoro-3,5-dichlorobenzonitrile was actually obtained. The yield was 98.3% and the purity was 98.6%.

Example 3

50 g of pentachlorobenzonitrile, 350 g of 2,4,6-trifluoro-3,5-dichlorobenzonitrile, 50 g of potassium fluoride and 7.5 g of 18-crown-6 were added into a 500 ml dry reaction bottle, stirred, heated to 170~180° C., preserved and reacted for 16 h, the reaction was stopped and cooled. When the internal temperature was dropped to less than 80° C., vacuum distillation was carried out until the system was completely evaporated to dryness, so as to obtain 390.3 g of 2,4,6-trifluoro-3,5-dichlorobenzonitrile. After the solvent was removed, 40.3 g of 2,4,6-trifluoro-3,5-dichlorobenzonitrile was actually obtained. The yield was 98.2% and the purity was 99.3%.

Example 4

55 g of pentachlorobenzonitrile, 330 g of 2,4,6-trifluoro-3,5-dichlorobenzonitrile and 51.3 g of potassium fluoride were added into a 500 ml dry reaction, bottle, stirred, heated to 230~240° C., preserved and reacted for 15 h, the reaction was stopped and cooled. When the internal temperature was dropped to less than 80° C., vacuum distillation was carried out until the system was completely evaporated to dryness, so as to obtain 374.5 g of 2,4,6-trifluoro-3,5-dichlorobenzonitrile. After the solvent was removed, 44.5 g of 2,4,6-trifluoro-3,5-dichlorobenzonitrile was actually obtained. The yield was 98.6% and the purity was 99.2%.

Example 5

60 g of pentachlorobenzonitrile, 330 g of 2,4,6-trifluoro-3,5-dichlorobenzonitrile, 51.5 g of potassium fluoride and 3 g of tetraphenylphosphonium bromide were added into a 500 ml dry reaction bottle, stirred, heated to 190-200° C., preserved and reacted for 12 h, the reaction was stopped and cooled. When the internal temperature was dropped to less than 80° C., vacuum distillation, was carried, out until the system was completely evaporated to dryness, so as to obtain 378.5 g of 2,4,6-trifluoro-3,5-dichlorobenzonitrile. After the solvent was removed, 48.5 g of 2,4,6-trifluoro-3,5-dichlorobenzonitrile was actually obtained. The yield was 98.5% and the purity was 99.4%.

Example 6

65 g of pentachlorobenzonitrile, 325 g of 2,4,6-trifluoro-3,5-dichlorobenzonitrile, 52 g of potassium fluoride, 1.3 g of 18-crown-6 and 1.3 g of tetraphenylphosphonium bromide were added into a 500 ml dry reaction bottle, stirred, heated to 220~230° C., preserved and reacted for 12 h, the reaction was stopped and cooled. When the internal temperature was dropped to less than 80° C., vacuum distillation was carried out until the system was completely evaporated to dryness, so as to obtain 377.6 g of 2,4,6-trifluoro-3,5-dichlorobenzonitrile. After the solvent was removed, 52.6 g of 2,4,6-trifluoro-3,5-dichlorobenzonitrile was actually obtained. The yield was 98.6% and the purity was 99.3%.

Example 7

50 g of pentachlorobenzonitrile, 720 g of 2,4,6-trifluoro-3,5-dichlorobenzonitrile, 44.3 g of sodium fluoride and 15 g of 15-crown-5 were added into a 1 L dry reaction bottle, stirred, heated to 210~220° C., preserved and reacted for 18 h, the reaction was stopped and cooled. When the internal temperature was dropped to less than 80° C., vacuum distillation was carried out until the system was completely evaporated to dryness, so as to obtain 760.3 g of 2,4,6-trifluoro-3,5-dichlorobenzonitrile. After the solvent was removed, 40.3 g of 2,4,6-trifluoro-3,5-dichlorobenzonitrile was actually obtained. The yield was 98.2% and the purity was 98.8%.

Example 8

40 g of pentachlorobenzonitrile, 360 g of 2,4,6-trifluoro-3,5-dichlorobenzonitrile, 32 g of sodium fluoride and 16 g of tetrabutyl ammonium chloride were added into a 500 ml dry reaction bottle, stirred, heated to 210~220° C., preserved and reacted for 18 h, the reaction was stopped and cooled. When the internal temperature was dropped to less than 80° C., vacuum distillation was carried out until the system was completely evaporated to dryness, so as to obtain 392.3 g of 2,4,6-trifluoro-3,5-dichlorobenzonitrile. After the solvent was removed, 32.3 g of 2,4,6-trifluoro-3,5-dichlorobenzonitrile was actually obtained. The yield was 98.4% and the purity was 98.7%.

Example 9

30 g of pentachlorobenzonitrile, 360 g of 2,4,6-trifluoro-3,5-dichlorobenzonitrile, 15.2 g of potassium fluoride, 1.2 g of triphenylmethyl phosphonium bromide and 1.2 g of tetrabutyl ammonium chloride were added into a 500 ml dry reaction bottle, stirred, heated to 200~210° C., preserved and reacted for 10 h, the reaction was stopped and cooled. When the internal temperature was dropped to less than 80° C., vacuum distillation was carried out until the system was completely evaporated to dryness, so as to obtain 384.2 g of 2,4,6-trifluoro-3,5-dichlorobenzonitrile. After the solvent was removed, 24.2 g of 2,4,6-trifluoro-3,5-dichlorobenzonitrile was actually obtained. The yield was 98.3% and the purity was 99.0%.

Example 10

60 g of 2,4,6-trifluoro-3,5-dichlorobenizonitrile, 160 g of formic acid and 0.3 g of 10% dry palladium carbon were added into a 250 ml autoclave, the autoclave was closed, nitrogen was used to displace the gas for three times, then hydrogen was used to displace the gas for five times, the pressure in the autoclave was controlled to 1.5~1.7 MPa using hydrogen, and hydrogenation reaction, was carried, out at 30~35° C. for 12 h. The reaction liquid was filtered to recover palladium carbon, the filtrate was concentrated at reduced pressure to remove formic acid, 100 g of water was added and then stirred at room temperature, 30 % sodium hydroxide solution was dropwise added to adjust the pH to be alkaline, and an, organic phase was separated by standing. 55.4 g of colorless clear liquid was obtained via vacuum rectification, which is 2,4,6-trifluoro-3,5-dichlorobenzylamine. The yield was 90.7%, and purity was 99.5%.

Example 11

45 g of 2,4,6-trifluoro-3,5-dichlorobenzonitrile, 315 g of acetic acid and 2.3 g of 5% dry palladium carbon were added into a 500 ml autoclave, the autoclave was closed, nitrogen was used to displace the gas for three times, then hydrogen was used to displace the gas for five times, the pressure in the autoclave was controlled to 0~0.2 MPa using hydrogen, and hydrogenation reaction was carried out at 50~55° C. for 4 h. The reaction liquid was filtered to recover palladium carbon, the filtrate was concentrated, at reduced pressure to remove acetic acid, 60 g of water was added and then stirred at room temperature, the pH was adjusted to be alkaline using 30% potassium carbonate solution, and an organic phase was separated by standing. 41.0 g of colorless clear liquid was obtained via vacuum rectification, which is 2,4,6-trifluoro-3,5-dichlorobenzylamine. The yield was 89.5%, and purity was 99.7%.

Example 12

30 g of 2,4,6-trifluoro-3,5-dichlorobenzonitrile 150 g of propionic acid and 6 g of 5% wet palladium carbon were added into a 250 ml autoclave, the autoclave was closed, nitrogen was used to displace the gas for three times, then hydrogen was used to displace the gas for five times, the pressure in the autoclave was controlled to 1.0~1.2 MPa using hydrogen, and hydrogenation reaction was carried out at 10~15° C. for 8 h. The reaction liquid was filtered to recover palladium carbon, the filtrate was concentrated, at reduced pressure to remove acetic acid, 60 g of water was added and then stirred at room temperature, the pH was adjusted to be alkaline using 20% potassium hydroxide solution, 50 g of dichloromethane was added, an organic phase was separated by, standing, a water phase was extracted using 30 g of dichloromethane, organic phases were combined, dichloromethane was removed by distillation. The concentrated liquid was rectified at reduced pressure to obtain 27.6 g of colorless clear liquid, which is 2,4,6-trifluoro-3,5-dichlorobenzylamine. The yield was 90.4%, and purity was 99.3%.

Example 13

35 g of 2,4,6-trifluoro-3,5-dichlorobenzonitrile, 350 g of iso-butyric acid and 1.8 g of 10% wet palladium carbon were added into a 500 ml autoclave, the autoclave was closed, nitrogen was used to displace the gas for three times, then hydrogen was used to displace the gas for five times, the pressure in the autoclave was controlled to 2.5~2.7 MPa using hydrogen, and hydrogenation reaction was carried out at 0~5° C. for 16 h. The reaction liquid was filtered to recover palladium carbon, the filtrate was concentrated at reduced pressure to remove iso-butyric acid, 80 g of 20% sodium carbonate solution was added and then stirred for 1 h at room temperature, a lower-layer, organic phase was separated by standing, a water phase was extracted using 30 g of ethyl, acetate, organic phases were combined, ethyl acetate was removed by distillation. The concentrated liquid was rectified at reduced pressure to obtain 32.4 g of colorless clear liquid, which is 2,4,6-trifluoro-3,5-dichlorobenzylamine. The yield was 90.9%, and purity was 99.4%.

Example 14

30 g of 2,4,6-trifluoro-3,5-dichlorobenzonitrile, 360 g of isopentanoic acid and 3 g of 1% dry palladium carbon were added into a 500 ml autoclave, the autoclave was closed, nitrogen was used to displace the gas for three times, then, hydrogen was used to displace the gas for five times, the pressure in the autoclave was controlled to 2.0~2.2 MPa using hydrogen, and hydrogenation reaction was carried out at 20~25° C. for 12 h. The reaction liquid was filtered to recover, palladium carbon, the filtrate was concentrated at reduced pressure to remove isopentanoic acid, 100 g of 15% sodium hydroxide solution was added and then stirred for 0.5 h at room temperature, a lower-layer organic phase was separated by standing, a water phase was extracted using 30 g of ethyl acetate, organic phases were combined, 32.4 g of colorless clear liquid was obtained via reduced, pressure rectification and 2,4,6-trifluoro-3,5-dichlorobenzylamine. The yield was 89.7%, and purity was 99.6%.

Example 15

22.6 g of 2,4,6-trifluoro-3,5-dichlorobenzonitrile, 320 g of propionic acid and 5.6 g of 1% wet palladium carbon were added into a 500 ml autoclave, the autoclave was closed, nitrogen was used to displace the gas for three times, then hydrogen was used to displace the gas for five times, the pressure in the autoclave was controlled to 0.5~0.6 MPa using hydrogen, and hydrogenation reaction was carried out at 40~45° C. for 8 h. The reaction liquid was filtered to recover palladium carbon, the filtrate was concentrated at reduced pressure to remove propionic acid, 75 g of water was, added and then stirred at room temperature, the pH was adjusted to be alkaline using solid sodium hydroxide, and an organic phase was separated by standing. 27.6 g of colorless clear liquid was obtained via vacuum rectification, which was 2,4,6-trifluoro-3,5-dichlorobenzylamine. The yield was 90.0%, and purity was 99.5%.

Example 16

60 g of 2,4,6-trifluoro-3,5-dichlorobenzylamine 90 g of methyl alcohol, 58 g of triethylamine and 3 g of 5% dry palladium carbon were added into a 250 ml autoclave, the autoclave was closed, nitrogen was used to displace the gas for three times, then hydrogen was used to displace the gas for five times, the pressure in the autoclave was controlled, to 0.7~0.8 MPa using hydrogen, and hydrogenation reaction was carried out at 20~25° C. for 10 h The reaction liquid was filtered to recover palladium carbon, the filtrate was concentrated at reduced pressure to remove acetic acid, 100 g of water was added and then stirred at room temperature, an organic phase was separated by standing and layering. 39.4 g of colorless clear liquid was obtained via rectification and was 2,4,6-trifluorobenzylamine. The yield was 93.4%, and purity was 99.6%.

Example 17

80 g of 2,4,6-trifluoro-3,5-dichlorobenzylamine, 300 g of water, 29.2 g of sodium hydroxide and 20 g of spongy nickel were added into a 500 ml autoclave, the autoclave was closed, nitrogen was used to displace the gas for three times, then hydrogen was used to displace the gas for five times, the pressure in the autoclave was controlled to 1.0~1.2 MPa using hydrogen, and hydrogenation reaction was carried out at 50~55° C. for 7 h. The reaction liquid was filtered, and an organic phase was separated by standing the filtrate. 52.0 g of colorless clear liquid was obtained via rectification, which was 2,4,6-trifluorobenzylamine. The yield was 92.8%, and purity was 99.7%.

Example 18

70 g of 2,4,6-trifluoro-3,5-dichlorobenzylamine, 560 g of ethanol, 13.5 g of magnesium oxide and 2.1 g of 10% dry palladium carbon were added into a 1 L autoclave, the autoclave was closed, nitrogen was used to displace the gas for three times, then hydrogen was used to displace the gas for five times, the pressure in the autoclave was controlled, to 1.5~1.7 MPa using hydrogen, and hydrogenation reaction was carried out at 60~65° C. for 6 h. The reaction liquid was filtered, the filtrate was concentrated at reduced pressure, the concentrated liquid was rectified to obtain 45.7 g of colorless clear liquid which was 2,4,6-trifluorobenzylamine. The yield was 93.2%, and purity was 99.5%.

Example 19

50 g of 2,4,6-trifluoro-3,5-dichlorobenzylamine, 600 g of water, 69 g of potassium phosphate and 5 g of spongy nickel were added into a 1 L autoclave, the autoclave was closed, nitrogen was used to displace the gas for three times, then hydrogen was used to displace the gas for five times, the pressure in the autoclave was controlled to 2.5~2.7 MPa using hydrogen, and hydrogenation reaction was carried out at 30~35° C. for 12 h. The reaction liquid was filtered, an organic phase was separated by standing the filtrate. 32.4 g of colorless clear liquid was obtained via rectification, which was 2,4,6-trifluorobenzylamine. The yield was 92.5%, and purity was 99.6%.

Example 20

75 g of 2,4,6-trifluoro-3,5-dichlorobenzylamine, 225 g of iso-butanol, 91 g of triethylene diamine and 3.7 g of 1% dry palladium carbon were added into a 500 ml autoclave, the autoclave, was closed, nitrogen was used to displace the gas for three times, then hydrogen was used to displace the gas for five times, the pressure in the autoclave was controlled to 0.1~0.2 MPa using hydrogen, and hydrogenation reaction was carried out at 80~85° C. for 5 h. The reaction liquid was filtered, the filtrate was concentrated at reduced pressure, the concentrated liquid was rectified to obtain 49.1 g of colorless clear liquid which was 2,4,6-trifluorobenzylamine. The yield was 93.5%, and purity was 99.7%.

Example 21

85 g of 2,4,6-trifluoro-3,5-dichlorobenzylamine, 425 g of isopropanol, 87.7 g of pyridine and 21 g of 1% wet palladium carbon were added into a 1 L autoclave, the autoclave was closed, nitrogen was used to displace the gas for three times, then hydrogen was used to displace the gas for five times, the pressure in the autoclave was controlled to 0.5~0.6 MPa using hydrogen, and hydrogenation reaction was carried out at 10~15° C. for 8 h. The reaction liquid was filtered, the filtrate was concentrated at reduced pressure, 100 g of water was added and stirred at room temperature, and an organic phase was separated by standing. 55.4 g of colorless clear liquid was obtained via rectification, which was 2,4,6-trifluorobenzylamine. The yield was 93.0%, and purity was 99.5%.

Example 22

90 g of 2,4,6-trifluoro-3,5-dichlorobenzylamine, 540 g of n-propanol, 138.5 g of N-methylmorpholine and 18 g of 5% wet palladium carbon were added into a 1 L autoclave, the autoclave was closed, nitrogen was used to displace the gas for three times, then hydrogen was used to displace the gas for five times, the pressure in the autoclave was controlled to 0.3~0.4 MPa using hydrogen, and hydrogenation reaction was carried out at 30~35° C. for 4 h. The reaction liquid was filtered, the filtrate was concentrated at reduced pressure, the concentrated liquid was rectified to obtain 59.1 g of colorless clear liquid which was 2,4,6-trifluorobenzylamine. The yield was 93.7%, and purity was 99.7%.

Example 23

35 g of 2,4,6-trifluoro-3,5-dichlorobenzonitrile, 650 g of acetic acid and 3.5 g of 10% dry palladium carbon were added into a 1 L autoclave, the autoclave was closed, nitrogen was used to displace the gas for three times, then hydrogen was used to displace the gas for five times, the pressure in the autoclave was controlled to 0.7~0.8 MPa using hydrogen, and hydrogenation reaction was carried out at 20~25° C. for 4 h. The reaction liquid was concentrated at reduced pressure to remove acetic acid, 70 g of water was added and stirred at room temperature, and the pH was adjusted to 8~9 using 20% potassium hydroxide solution for later use.

The above materials were placed into a 500 ml autoclave, 60 g of 30% potassium hydroxide was added, the autoclave was closed, nitrogen was used to displace the gas for three times, then hydrogen was used to displace the gas for five times, the pressure in the autoclave was controlled to 2.5~2.7 MPa using hydrogen, and hydrogenation reaction was carried out at 60~65° C. for 10 h. The reaction liquid was filtered, an organic phase was separated by standing the filtrate, and 22.1 g of 2,4,6-trifluorobenzylamine was obtained via rectification. The yield was 88.6%, and purity was 99.6%.

Example 24

50 g of 2,4,6-trifluoro-3,5-dichlorobenzonitrile, 300 g of propionic acid and 7.5 g of 5% dry palladium carbon were added into a 500 ml autoclave, the autoclave was closed, nitrogen was used to displace the gas for three times, then hydrogen was used to displace the gas for five times, the pressure in the autoclave was controlled to 1.3~1.5 MPa using hydrogen, and hydrogenation reaction was carried out at 10~15° C. for 5 h. The reaction liquid was filtered, the filtrate was concentrated at reduced pressure, 75 g of water was added and stirred at room temperature, the pH was adjusted to be alkaline using 20% potassium carbonate solution, and an organic phase was separated by standing for later use.

The above organic phases were placed into a 500 ml autoclave, 200 g of ethanol, 67 g of triethylamine and 6 g of 10% wet palladium carbon were added, the autoclave was closed, nitrogen was used to displace the gas for three times, then hydrogen was used to displace the gas for five times, the pressure in the autoclave was controlled to 1.0~1.2 MPa using hydrogen, and hydrogenation reaction was carried out at 30~35° C. for 5 h. The reaction liquid was filtered, the filtrate was concentrated at reduced pressure, the concentrated liquid was rectified to obtain 31.7 g of 2,4,6-trifluorobenzylamine. The yield was 88.9%, and the purity was 99.5%.

Example 25

45 g of 2,4,6-trifluoro-3,5-dichlorobenzonitrile, 315 g of n-butyric acid and 4.5 g of 10% dry palladium carbon were added into a 500 ml autoclave, the autoclave was closed, nitrogen was used to displace the gas for three times, then hydrogen was used to displace the gas for five times, the pressure in the autoclave was controlled to 0.3~0.4 MPa using hydrogen, and hydrogenation reaction was carried out at 30~35° C. for 5 h. The reaction liquid was filtered, the filtrate was concentrated at reduced pressure to remove n-butyric acid, 180 g of water was added and stirred at room temperature, the pH was adjusted to be alkaline using sodium potassium hydroxide solid, and an organic phase was separated by standing for later use.

The above organic phases were placed into a 500 ml autoclave, 250 g of methanol, 12 g of magnesium oxide and 4.5 g of 5% wet palladium carbon were added, the autoclave was closed, nitrogen was used to displace the gas for three times, then hydrogen was used to displace the gas for five times, the pressure in the autoclave was controlled to 0.2~0.3 MPa using hydrogen, and hydrogenation reaction was carried out at 20~25° C. for 6 h. The reaction liquid was filtered, the filtrate was concentrated at reduced pressure, the concentrated liquid was rectified to obtain 28.8 g of colorless clear liquid which was 2,4,6-trifluorobenzylamine. The yield was 89.8%, and the purity was 99.7%.

Example 26

35 g of 2,4,6-trifluoro-3,5-dichlorobenzonitrile, 315 g of n-pentanoic acid and 1.5 g of 5% wet palladium carbon were added into a 500 ml autoclave, the autoclave was closed, nitrogen was used to displace the gas for three times, then hydrogen was used to displace the gas for five times, the pressure in the autoclave was controlled to 0.8~1.0 MPa using hydrogen, and hydrogenation reaction was carried out at 20~25° C. for 10 h. The reaction liquid was concentrated at reduced pressure to remove n-pentanoic acid, 160 g of water was added and stirred at room temperature, and the pH was adjusted to 9~10 using 30% sodium hydroxide solution for later use.

The above materials were placed into a 500 ml autoclave, 48 g of potassium carbonate and 7 g of spongy nickel were added, the autoclave was closed, nitrogen was used to displace the gas for three times, then hydrogen was used to displace the gas for five times, the pressure in the autoclave was controlled to 1.5~1.7 MPa, using hydrogen, and hydrogenation reaction was carried out at 40~45° C. for 10 h. The reaction liquid was filtered, and an organic phase was separated by standing the filtrate. 22.3 g of colorless clear liquid was obtained via rectification, which was 2,4,6-trifluorobenzylamine. The yield was 89.4%, and the purity was 99.6%.

Comparative Example 1

65 g of pentachlorobenzonitrile, 325 g of N,N-dimethylformamide, 52 g of potassium fluoride, 1.3 g of 18-crown-6 and 1.3 g of tetraphenylphosphonium bromide were added into a 500 ml dry reaction bottle, stirred, heated to 130-140° C., preserved and reacted for 5 h, the reaction was stopped and cooled. When the internal temperature was dropped to less than 40° C., vacuum distillation was carried out until the system was completely evaporated to dryness, the obtained fraction was, rectified at reduced pressure to remove the solvent, the concentrated liquid was further rectified to obtain 49.5 g of colorless clear liquid which was 2,4,6-trifluoro-3,5-dichlorobenzonitrile. The yield was 92.8% and the purity was 99.1%.

Comparative Example 2

65 g of pentachlorobenzonitrile, 325 g of sulfolane, 52 g of potassium fluoride, 1.3 g of 18-crown-6 and 1.3 g of tetraphenylphosphonium bromide were added into a 500 ml dry reaction bottle, stirred, heated to 150-160° C., preserved and reacted for 8 h, the reaction was stopped and cooled. When the internal temperature was dropped to less than 80° C., vacuum distillation was carried out until the system was completely evaporated to dryness, and the obtained fraction was rectified at reduced pressure to obtain 47.8 g of colorless clear liquid which was 2,4,6-trifluoro-3,5-dichlorobenzonitrile. The yield was 89.6% and the purity was 98.9%.

Comparative Example 3

65 g of pentachlorobenzonitrile, 325 g of N-methylpyrlidone, 52 g of potassium fluoride, 1.3 g of 18-crown-6 and 1.3 g of tetraphenylphosphonium bromide were added into a 500 ml dry reaction bottle, stirred, heated to 140~150° C., preserved and reacted for 6 h, the reaction was stopped and cooled. When the internal temperature was dropped to less than 80° C., vacuum distillation was carried out until the system was completely evaporated to dryness, the obtained fraction was added into 400 g of water and stirred for 10 min at room temperature, an organic phase was separated by standing, and drying was carried out using anhydrous sodium sulfate to obtain 49.7 g of colorless clear liquid which was 2,4,6-trifluoro-3,5-dichlorobenzonitrile. The yield was 93.2% and the purity was 98.3%.

Comparative Example 4

50 g of 2,4,6-trifluror-dichlorobenzonitrile, 200 g of ethanol, 67 g of triethvlarnine and 6 g of 10% wet palladium carbon were added into a 500 ml dry reaction bottle, the autoclave was closed, nitrogen was used to displace the gas for three times, then hydrogen was used to displace the gas for five times, the pressure in the autoclave was controlled to 1.0~1.2 MPa using hydrogen, and hydrogenation reaction was carried out at 10~15° C. for 5 h. Sampling analysis was carried out, and raw materials disappear. The reaction liquid was filtered, the filtrate was concentrated at reduced pressure, 75 g of water was added and stirred at room temperature, the pH was adjusted to be alkaline using 20% potassium carbonate solution, and an organic phase was separated by standing. 12.5 g of colorless clear liquid was obtained via rectification, which was 2,4,6-trifluorobenzylamine. The yield was 35.1%, and the purity was 98.3%.

Comparative Example 5

50 g of 2,4,6-trifluoro-3,5-dichlorobenzonitrile, 200 g of ethyl acetate, 67 g of triethylamine and 6 g of 10% wet palladium carbon were added into a 500 ml autoclave, the autoclave, was closed, nitrogen was used to displace the gas for three times, then hydrogen was used to displace the gas for five times, the pressure in the autoclave was controlled to 1.0~1.2 MPa using hydrogen, and hydrogenation reaction was carried out at 60~65° C. for 8 h. Sampling analysis was earned out, and raw materials disappear. The reaction liquid was filtered, and the filtrate was concentrated at reduced pressure to obtain 2,4,6-trifluorobenzonitrile crude product.

The 2,4,6-trifluorobenzonitrile crude product was placed into the 500 ml autoclave, 300 g of propionic acid and 7.5 g of 5% dry palladium carbon were added, the autoclave was closed, nitrogen was used to displace the gas for three times, then hydrogen was used to displace the gas for five times, the pressure in the autoclave was controlled to 1.3~1.5 MPa using hydrogen, and hydrogenation reaction was carried out at 10~15° C. for 5 h. Sampling analysis was carried out, and raw materials disappear. The reaction liquid was filtered, the filtrate was concentrated at reduced pressure, 75 g of water was added and stirred at room temperature, the pH was adjusted to be alkaline using 20% potassium carbonate solution, and an organic phase was separated by standing. 14.0 g of colorless clear liquid was obtained via rectification, which was 2,4,6-trifluorobenzylamine. The yield was 39.3%, and purity was 98.5%.

Comparative Example 6

50 g of 2,4,6-trifluoro-3,5-dichlorobenzonitrile 200 g of ethanol, 67 g of triethylamine and 6 g of 10% wet palladium carbon were added into a 500 ml autoclave, the autoclave was closed, nitrogen was used to displace the gas for three times, then hydrogen was used to displace the gas for five times, the pressure in the autoclave was controlled to 1.5~1.7 MPa using hydrogen, and hydrogenation reaction was carried out at 30~35° C. for 24 h. Sampling analysis was carried out, and raw materials disappear. The reaction liquid was filtered, and the filtrate was concentrated at reduced pressure, and the concentrated liquid was rectified to obtain 6.2 g of colorless clear liquid which was 2,4,6-trifluorobenzylamine. The yield was 17.4%, and the purity was 96.8%.

We claim:

1. A synthesis method of 2,4,6-trifluorobenzylamine, comprising the following steps:
   (1) allowing pentachlorobenzonitrile as a raw material to undergo fluoridation reaction with a fluoridation agent based on 2,4,6-trifluoro-3,5-dichlorobenzonitrile as a solvent to obtain 2,4,6-trifluoro-3,5-dichlorobenzonitrile;
   (2) hydrogenating the obtained 2,4,6-trifluoro-3,5-dichlorobenzonitrile with hydrogen in the presence of organic carboxylic acid based on palladium carbon as a catalyst to obtain 2,4,6-trifluoro-3,5-dichlorobenzylamine;
   (3) hydrogenating 2,4,6-trifluoro-3,5-dichlorobenzylamine obtained in step (2) with hydrogen in a solvent in the presence of a catalyst to obtain 2,4,6 -trifluorobenzylamine.

2. The synthesis method of 2,4,6-trifluorobenzylamine according to claim 1, wherein in step (1), the amount of 2,4,6-trifluoro-3,5-dichlorobenzonitrile used as the solvent is 1~15 times the mass of pentachlorobenzonitrile.

3. The synthesis method of 2,4,6-trifluorobenzylamine according to claim 1, wherein in step (1), the fluoridation agent is selected from one or two of sodium fluoride and potassium fluoride, and the molar ratio of the fluoridation agent to pentachlorobenzonitrile is (3:1)~(6:1).

4. The synthesis method of 2,4,6-trifluorobenzylamine according to claim 1, wherein in step (1), the reaction temperature is 170~240° C.

5. The synthesis method of 2,4,6-trifluorobenzylamine according to claim 1, wherein in step (2), the organic carboxylic acid is selected from one or more of formic acid, acetic acid, propionic acid, n-butyric acid, iso-butyric acid, n-pentanoic acid and iso-pentanoic acid, the organic carboxylic acid is used as not only acid but also a solvent, and the amount of the organic carboxylic acid is 1~20 times the mass of 2,4,6-trifluoro-3,5-dichlorobenzonitrile.

6. The synthesis method of 2,4,6-trifluorobenzylamine according to claim 1, wherein in step (2), the pressure of hydrogenation is 0.01~3.0 MPa.

7. The synthesis method of 2,4,6-trifluorobenzylamine according to claim 1, wherein in step (2), the reaction temperature is 0~70° C.

8. The synthesis method of 2,4,6-trifluorobenzylamine according to claim 1, wherein in step (3), the solvent is selected from one or more of water, methanol, ethanol, n-propanol, iso-propanol, n-butanol, iso-butanol and tert-butanol, and the amount of the solvent is 1~15 times the mass of 2,4,6-trifluoro-3,5-dichlorobenzylamine.

9. The synthesis method of 2,4,6- rifluorobenzylarnine according to claim 1, wherein in step (3), the catalyst is selected from one or two of palladium carbon and spongy nickel.

10. The synthesis method of 2,4,6-trifluorobenzylamine according to claim 1, wherein in step (3), the pressure of hydrogenation is 0.01~3.0 MPa.

11. The synthesis method of 2,4,6-trifluorobenzylamine according to claim 1, wherein in step (3), the reaction temperature is 0~100° C.

* * * * *